United States Patent [19]

Aoki et al.

[11] Patent Number: 4,746,748

[45] Date of Patent: May 24, 1988

[54] METHOD FOR REDUCING HYDROXOCOBALT (III) SCHIFF BASE COMPLEX

[75] Inventors: Kunihiro Aoki, Tokyo; Shunsuke Minami, Kanagawa, both of Japan

[73] Assignee: Mitsubishi Rayon Co., Ltd., Tokyo, Japan

[21] Appl. No.: 941,125

[22] Filed: Dec. 12, 1986

[30] Foreign Application Priority Data

Dec. 13, 1985 [JP] Japan .................................. 60-280783
Dec. 13, 1985 [JP] Japan .................................. 60-280784

[51] Int. Cl.$^4$ ............................................. C07F 15/06
[52] U.S. Cl. ........................................ 556/34; 556/32; 556/35
[58] Field of Search ............................. 556/35, 32, 34

[56] References Cited

U.S. PATENT DOCUMENTS

| | | | |
|---|---|---|---|
| 3,248,410 | 4/1966 | Berenbaum | 556/32 |
| 3,472,876 | 10/1969 | Klein | 556/32 X |
| 3,636,007 | 1/1972 | Calderazzo | 556/32 X |
| 3,701,660 | 10/1972 | Pratt et al. | 556/32 X |
| 3,803,192 | 4/1974 | Neri et al. | 556/35 X |
| 3,809,632 | 5/1974 | Costa et al. | 556/35 |
| 3,901,939 | 8/1975 | Neri et al. | 556/32 X |
| 4,032,617 | 6/1977 | Gay | 556/32 X |

*Primary Examiner*—Paul F. Shaver
*Attorney, Agent, or Firm*—Sughrue, Mion, Zinn, Macpeak & Seas

[57] ABSTRACT

A method is described for reducing a hydroxocobalt (III) Schiff base complex to a cobalt (II) Schiff base complex by heating the former complex to a temperature below the decomposition point of the latter complex.

11 Claims, No Drawings

METHOD FOR REDUCING HYDROXOCOBALT (III) SCHIFF BASE COMPLEX

FIELD OF THE INVENTION

The present invention relates to a simple and efficient method for reducing a hydroxocobalt (III) Schiff base complex into a cobalt (II) Schiff base complex.

BACKGROUND OF THE INVENTION

Cobalt (II) Schiff base complexes have been used as oxidation catalysts and for the selective enrichment of oxygen by making use of their ability to adsorb and desorb oxygen. However, if these complexes are brought into contact with protic compounds such as water or alcohols in the presence of oxygen, they are irreversibly oxidized to hydroxocobalt (III) Schiff base complexes which have little or no ability to serve as catalysts or to adsorb and desorb oxygen.

In response to this problem, attempts have been made to reactivate the hydroxocobalt (III) Schiff base complexes by reducing them into cobalt (II) Schiff base complexes. Nishinaga et al have proposed the use of alcohol as a reducing agent (see the preprint for the 34th Conference on Complex Salts sponsored by Japan Chemical Society, p.344, 1984).

However, the method of reducing hydroxocobalt (III) Schiff base complexes to cobalt (II) Schiff base complexes with an alcohol being used as a reducing agent has several disadvantages. First, the reducing agent is not reusable; also, in order to achieve a high reduction rate, this method requires the reducing agent to be used in a stoichiometrically excess amount, but the cobalt (II) Schiff base complex containing the residual reducing agent will not serve either as an oxidation catalyst or as an oxygen-adsorbing and desorbing medium, and hence must be freed of such excess reducing agent; furthermore, the hydroxocobalt (III) Schiff base complex has a fairly low solubility in alcohol, and thus a concentrated alcohol solution sufficient to be suitable for use in large-volume treatment cannot be prepared; still further, an additional step is necessary to separate the reduced complex from alcohol.

SUMMARY OF THE INVENTION

With a view to solving these problems, the present inventors conducted studies and found unexpectedly that the hydroxocobalt (III) Schiff base complex can be readily reduced to a cobalt (II) Schiff base complex by heating. The present invention has been accomplished on the basis of this finding.

An object, therefore, of the present invention is to overcome the problems associated with the prior art and to provide a simple and efficient method for reducing a hydroxocobalt (III) Schiff base complex to a cobalt (II) Schiff base complex without employing any reducing agent.

This object of the present invention can be achieved by heating a hydroxocobalt (III) Schiff base complex to a temperature lower than the decomposition point of a cobalt (II) Schiff base complex.

DETAILED DESCRIPTION OF THE INVENTION

The Schiff base as one component of the hydroxocobalt (III) Schiff base complex to the reduced by the method of the present invention may be of any class, but preferable examples are the reaction products of amines and salicylaldehyde, acetylacetone, o-hydroxyacetophenone, or derivatives thereof, with the reaction products of amines and salicylaldehyde or derivatives thereof being more preferable. Illustrative hydroxocobalt (III) Schiff base complexes wherein the Schiff base is made of the reaction products of amines and salicylaldehyde or derivatives thereof include: N,N'-ethylenebis (salicylideniminato)hydroxocobalt (III) complex represented by formula (I) set forth below (this compound in hereinafter referred to as hydroxocobalt (III) salen); N,N'-iminodi-n-propylbis(-salicylideniminato)hydroxocobalt (III) complex represented by formula (II) set forth below (this compound is hereinafter referred to as hydroxocobalt (III) salpro); derivatives of these compounds which are substituted by a methoxy group at 6 and 6' positions on the benzene ring; and derivatives of these compounds wherein the hydrogen atom of —CH=N< of the Schiff base portion is substituted by an alkyl group (e.g., a methyl group, an ethyl group, etc.), a phenyl group, an allyl group (e.g., a benzyl group, etc.), etc.

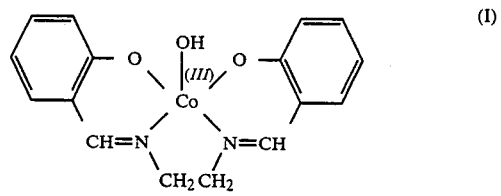

(I)

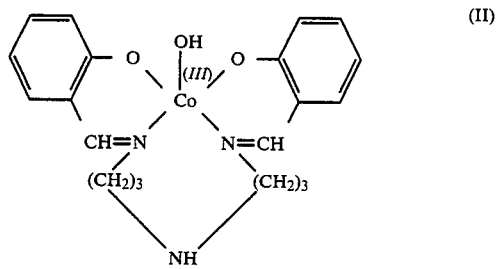

(II)

In the method of the present invention wherein the hydroxocobalt (III) Schiff base complex is reduced by heating, the complex must not be heated to a temperature equal to or above the decomposition point of the cobalt (II) Schiff base complex which is the reduced form of said complex. Otherwise, the cobalt (II) Schiff base complex will decompose, and the decomposition product will reduce the purity of the complex no matter how short the period of heating is.

The hydroxocobalt (III) Schiff base complex to be reduced by the method of the present invention may be in a solid state or in solution.

If the complex is reduced in a solid state, it may take on any form, but, from the viewpoint of the need to achieve uniform reaction and high thermal efficiency, a fine particulate form is preferable. If desired, the hydroxocobalt (III) Schiff base complex may be present in combination with other types of solids, such as polystyrene, polymethyl methacrylate, polyamide, polyimido, polyester, polysiloxane, polyvinylidene fluoride, polytetrafluoroethylene, glass, or metal.

Heating in a solid state may be effected in any kind of atmosphere, such as air, vacuum, or inert gas. However, since most of the cobalt (II) Schiff base complexes produced are highly reactive with oxygen, an oxygen-free atmosphere is preferable. Heating in a solid state may be conducted in the presence of oxygen if binding of the cobalt (II) Schiff base complex with oxygen is not prohibited, for example, the cobalt (II) Schiff base complex is used for adsorbing and desorbing oxygen.

Heating of the hydroxocobalt (III) Schiff base complex in a solid state is preferabley conducted at temperatures of 100° C. or above. If the temperature of heating is less than 100° C., the rate of reduction that can be achieved is slow and may be less suitable for practical applications.

If the hydroxocobalt (III) Schiff base complex is in solution, it can be satisfactorily reduced by heating at temperatures lower than those which are necessary to reduce the complex when it is in a solid state. However, if the complex is brought into contact with a protic compound in the presence of oxygen, the reduced form of the complex will return to the initial oxidized form through the reaction of the formation of a hydroxocobalt (III) Schiff base complex. Therefore, if reduction by heating is applied to a hydroxocobalt (III) Schiff base complex in solution, care must be taken to avoid the introduction of a protic compound into an oxygen-containing reaction system.

Any solvent may be employed if it is capable of dissolving the hydroxocobalt (III) Schiff base complex. As already mentioned, if the solvent used contains a protic compound, heating must be effected in a oxygen-free atmosphere. Illustrative solvents that may be employed with advantage are methylene chloride, dichloroethane, tetrachloroethane, acetonitrile, benzonitrile, dimethylformamide, dimethylacetoamide and dimethyl sulfoxide. The concentration of the hydroxocobalt (III) Schiff base complex in solution may assume any value so long as the complex is dissolved uniformly.

The hydroxocobalt (III) Schiff base complex in solution is heated to at least 30° C. in order to achieve the intended reduction. If the heating temperature is less than 30° C., the rate of reduction that can be achieved is slow and may be less suitable for practical purposes. In order to attain compromise between the efficiency of thermal energy and reduction rate, heating within the range of from 40° to 100° C. is preferable.

In the absence of any protic compound, the hydroxocobalt (III) Schiff base complex in solution may be heated in an oxygen-containing atmosphere such as air if the resulting cobalt (II) Schiff base complex is not easily reactive with oxygen to form a complex. However, if the resulting cobalt (II) Schiff base complex in solution is highly reactive to form a complex, heating is preferably conducted in an oxygen-free atmosphere. A cobalt (II) Schiff base complex in solution that readily reacts with oxygen to form a complex may be heated in the presence of oxygen if the formation of a complex with oxygen is not prohibited, for example, the cobalt (II) Schiff base complex is used for adsorbing and desorbing oxygen.

The following examples are provided for the purpose of further illustrating the present invention, but are in no way to be taken as limiting. In the following examples, samples of hydroxocobalt (III) salen were prepared in accordance with the method of Nishinaga et al. described on page 132 of the preprint for the 33rd Conference on Complex Salt Chemistry sponsored by Japan Chemical Society and subsequently dried in vacuo at 80° C. for 24 hours; samples of hydroxocobalt (III) salpro were also prepared and dried by essentially the same method.

EXAMPLE 1

A blackish brown powder of hydroxocobalt (III) salen (0.685 g) was heated in air at 220° C. for 20 minutes, whereupon the color of the powder turned to reddish brown. After completion of the heating, the powder was cooled to room temperature in a nitrogen atmosphere; the powder was found to weigh 0.652 g. An IR absorption spectrum of this powder and an elemental analysis fo the purified product obtained by re-precipitation from a methanol-water solvent showed that this powder was cobalt (II) salen having formula (III).

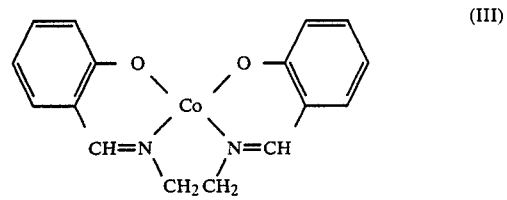

The starting point of the decomposition of cobalt (II) salen as measured by the thermobalance method as described in Shin Jitsuken Kagaku Kouza, Vol. 9-2, page 509 (published by Maruzen Co.) was approximately 335° C.

EXAMPLE 2

A blackish brown powder of hydroxocoblt (III) salpro (0.825 g) was heated in a nitrogen atmosphere at 145° C. for 25 minutes. After completion of the heating, the powder was cooled to room temperture in a nitrogen atmosphere; the powder was found to weight 0.790 g. The color of the powder had turned to dark yellowish brown. An IR absorption spectrum of this powder and an elemental analysis of the purified product obtained by dissolution and reprecipitation from methanol-water showed that this powder was cobalt (II) salpro having formula (IV).

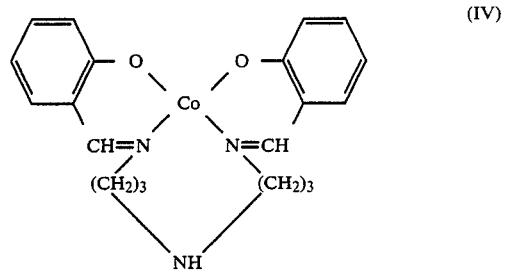

The starting point of the decomposition of cobalt (II) salpro as measured by the thermobalance method was approximately 315° C.

EXAMPLE 3

An acetonitrile solution of hydroxocobalt (III) salen ($5 \times 10^{-5}$ moles/liter) was heated at 70° C. in air with agitation. The progress of the reductive reaction as initiated by heating was monitored by observing the variation in absorbance at 409 nm in the UV absorption spectrum. Fifty minutes after start of the heating, the absorbance at 409 nm reached a value that was substantially equal to the absorbance of a acetonitrile solution of cobalt (II) salen of formula (III) having a concentration of $5 \times 10^{-5}$ moles/liter. This solution was concentrated and diethyl ether was added. The resulting dark brown precipitate was separated by filtration and dried under reduced pressure at 70° C. for 10 hours. An IR absorption spectrum of this precipitate and an elemental analysis of the purified product thereof showed that this precipitate was cobalt (II) salen.

COMPARATIVE EXAMPLE 1

An acetonitrile solution of hydroxocobalt (III) salen ($5 \times 10^{-5}$ moles/liter) was stirred at 10° C. in air. Forty-eight hours later, an IR absorption spectrum of the solution was recorded; the spectrum was little different from the initial record, suggesting that the progress of reduction that had occurred in the solution of hydroxocobalt (III) salen was substantially nil.

EXAMPLE 4

A solution of hydroxocobalt (III) salpro ($10^{-4}$ moles/liter) in 1,2-dichloroethane was heated at 60° C. in a nitrogen atmosphere with stirring. After the lapse of 60 minutes, the solution was concentrated and diethyl ether was added. The resulting yellowish brown precipitate was separated by filtration and dried under reduced pressure at 70° C. for 10 hours. An IR absorption spectrum of the precipitate and an elemental analysis of the purified product thereof showed that this precipitate was cobalt (II) salpro of formula (IV).

As described hereinbefore, in accordance with the present invention, a cobalt (II) Schiff base complex which has been deactivated to an ineffective hydroxocobalt (III) Schiff base complex form through oxidation in the presence of a protic compound such as water can be reduced to the initial form by a simple and efficient method that involves only the heating of said complex either in a solid state or in solution without employing any reducing agent. Heating of the hydroxocobalt (III) Schiff base complex in a solid state is more adapted to commercial applications, since this type of complex has a fairly low solubility in solvents and cannot be dissolved in sufficiently high concentrations to be suitable for use in large-scale treatments.

While the invention has been described in detail and with reference to specific embodiments thereof, it will be apparent to one skilled in the art that various changes and modifications can be made there in without departing from the spirit and scope thereof.

What is claimed is:
1. A method for reducing a hydroxocobalt (III) Schiff base complex to a cobalt (II) Schiff base complex by heating the former complex to a temperature below the decomposition point of the later complex.

2. A method according to claim 1, wherein the Schiff base which is one component of said hydroxocobalt (III) Schiff base complex is the reaction product of an amine and a compound selected from among salicylaldehyde, acetylacetone, o-hydroxyacetophenone, and derivatives thereof.

3. A method according to claim 2, wherein said Schiff base is ethylenebis(salicylideniminato), iminodi-n-propylbis(salicylideniminato), or a derivative thereof.

4. A method according to claim 1, wherein said hydroxocobalt (III) Schiff base complex exists in a solid state and is heated to a temperature of 100° C. or higher.

5. A method according to claim 1, wherein said hydroxocobalt (III) Schiff base complex is present in solution and is heated at a temperature of 30° C. or higher in the absence of oxygen.

6. A method according to claim 5, wherein said hydroxocobalt (III) Schiff base complex is dissolved in at least one solvent selected from among methylene dichloethane, tetrachloroethane, acetonitrile, benzonitrile, dimethylformamide, dimethylacetoamide and dimethyl sulfoxide.

7. A method according to claim 1, wherein said hydroxocobalt (III) Schiff base complex is present in solution in the absence of any protic compound and is heated to a temperature of 30° C. or higher.

8. A method according to claim 7, wherein said hydroxocobalt (III) Schiff base complex is dissolved in at least one solvent selected from among methylene dichloethane, tetrachloroethane, acetonitrile, benzonitrile, dimethylformamide, dimethylacetoamide and dimethyl sulfoxide.

9. A method according to claim 5, wherein said hydroxocobalt (III) Schiff base complex is heated to a temperature within the range of from 40° to 100° C.

10. A method according to claim 2, wherein the Schiff base which is one component of said hydroxocobalt (III) Schiff base complex is the reaction product of an amine and a salicylaldehyde or derivative thereof.

11. A method according to claim 7, wherein said hydroxocobalt (III) Schiff base complex is heated to a temperature within the range of from 40° to 100° C.

* * * * *